United States Patent
Perez et al.

(10) Patent No.: US 6,869,514 B1
(45) Date of Patent: Mar. 22, 2005

(54) RAPID ASSEMBLY CASTING SYSTEM FOR SLAB GELS

(75) Inventors: Evelio Perez, San Pablo, CA (US); George Fernwood, Larkspur, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 1015 days.

(21) Appl. No.: 09/696,537

(22) Filed: Oct. 25, 2000

Related U.S. Application Data

(62) Division of application No. 09/249,378, filed on Feb. 12, 1999, now Pat. No. 6,162,342.

(51) Int. Cl.[7] .............................................. C02F 1/469
(52) U.S. Cl. ..................... 204/606; 204/618; 204/619
(58) Field of Search ............................ 204/606, 619, 204/618

(56) References Cited

U.S. PATENT DOCUMENTS

| | | | |
|---|---|---|---|
| 4,325,796 A | | 4/1982 | Hoefer et al. |
| 4,518,476 A | | 5/1985 | Delony et al. |
| 4,574,040 A | | 3/1986 | Delony et al. |
| 4,773,984 A | | 9/1988 | Flesher et al. |
| 4,784,738 A | | 11/1988 | Sleeter et al. |
| 4,954,236 A | | 9/1990 | Kushner et al. |
| 5,112,470 A | * | 5/1992 | Sylvester .................. 204/618 |
| 5,284,565 A | | 2/1994 | Chu et al. |
| 5,540,498 A | | 7/1996 | Chu |
| 5,632,877 A | * | 5/1997 | Van Atta .................. 204/618 |
| 5,656,145 A | | 8/1997 | Nguyen et al. |
| 5,827,418 A | | 10/1998 | Haven et al. |
| 5,843,295 A | | 12/1998 | Steiner et al. |

FOREIGN PATENT DOCUMENTS

| | | |
|---|---|---|
| EP | 0 684 467 A1 | 11/1995 |
| EP | 0 339 975 A2 * | 11/1998 |
| GB | 2 184 238 A | 6/1987 |
| GB | 2 157 443 A | 10/1995 |
| JP | 5237125 A | 9/1993 |
| JP | 8233779 A | 9/1996 |
| JP | 8257984 A | 10/1996 |
| JP | 1062389 A | 3/1998 |
| JP | 10296072 A | 11/1998 |
| JP | 1128572 A | 2/1999 |
| WO | WO 97/22874 | 6/1997 |
| WO | WO 98/25136 | 6/1998 |
| WO | WO 98/52031 | 11/1998 |
| WO | WO 99/53305 | 10/1999 |

OTHER PUBLICATIONS

Run With It (Mini–Protean 3 info), Bulletin 2378, Bio–Rad Laboratories, Life Science Group.
Mini–Protean II Electrophoresis Cell, Instruction Manual.

* cited by examiner

*Primary Examiner*—Ling-Sui Choi
(74) *Attorney, Agent, or Firm*—M. Henry Heines; Townsend and Townsend and Crew, LLP

(57) ABSTRACT

Flat plates serving as molds and enclosures for slab gels are held together by a clamping frame in which the side edges of the plates slide into facing channels and are clamped by lever-operated cams that compress the channel walls against the plate surfaces. The joined plates are held on a vertical support rack containing a finger-operated spring-loaded notched clamp that presses down on the plates to seal the opening at the bottom edges of the plates against a gasket. A well-forming comb for insertion between the plates contains flexible outwardly angled fingers to seal against the spacers between the plates.

4 Claims, 5 Drawing Sheets

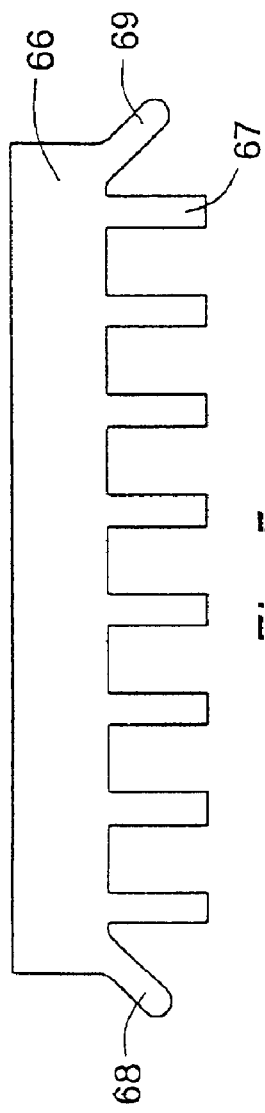
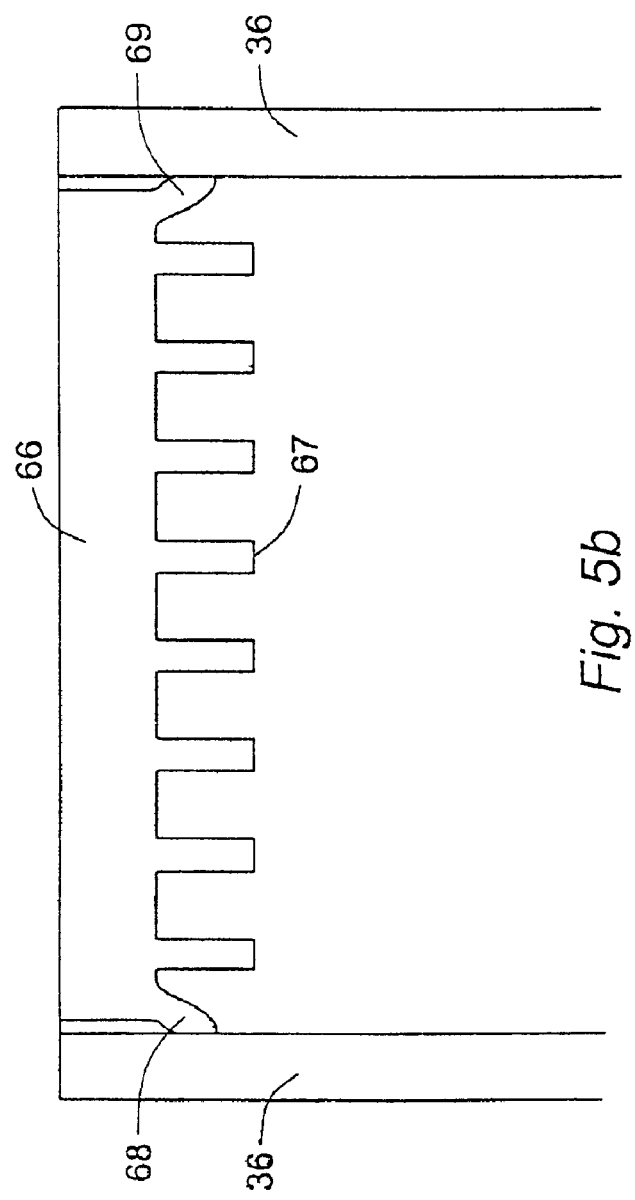
Fig. 5a
Fig. 5b

RAPID ASSEMBLY CASTING SYSTEM FOR SLAB GELS This is a Divisional application Ser. No. 09/249,378, filed Feb. 12, 1999, now U.S. Pat. No. 6,162,342.

This invention lies in the field of electrophoresis in slab-shaped gels, and particularly in the methods and types of apparatus used for casting slab-shaped gels from a liquid gel-forming solution.

BACKGROUND OF THE INVENTION

Electrophoresis in slab gels is widely used for separating and analyzing mixtures of chemical species, and particularly mixtures of complex species such as proteins, polypeptides, nucleic acids and oligonucleotides. Slab gels permit the simultaneous analysis of multiple samples as well as the inclusion of standards to facilitate the identification of the species. Once the separation has been performed, a slab gel is easily removed from its enclosure and readily stained for detection and analysis.

Electrophoresis gels are prepared by polymerization of monomers in liquid solutions. Some of the largest sources of operator error and loss of time in the laboratory with slab gel electrophoresis are in the preparation stages of the gel and particularly in the casting procedure. With many types of apparatus, it often difficult to achieve proper alignment and assembly of the parts in a leak-proof manner without damage or breakage. The procedure requires time-consuming care, particularly when performed by those who are inexperienced. The present invention seeks to address these difficulties.

SUMMARY OF THE INVENTION

This invention resides in several novel aspects of the structure and use of casting systems for slab gels. The various aspects are independently useful and can be included individually in gel casting systems or in combination.

One aspect of this invention is a cam-operated mounting frame for holding flat plates and spacers together in a fluid-tight enclosure. The side edges of the stacked glass plates (including spacers, which may be bonded to one of the plates or separate strips for insertion between the plates) slide into a pair of facing channels in a loose fit, and the walls of the channels are compressible against the plates by lever-operated cams that hold the plates and spacers against one another in a fluid-tight manner. Another aspect of the invention addresses the manner in which the joined plates are secured to a vertical support rack where gel-forming solution is placed in the gap between the plates and allowed to solidify and form the gel. In this aspect, the joined plates are held on a vertical support rack with the bottom opening of the plates pressed against the floor of the rack by a spring-loaded notched clamp at the top of the rack, the clamp being one that is readily opened and closed by a finger tab. A third aspect of the invention resides in a variation on the commonly used inserts or "combs" that are placed in the gel space to form sample wells in the gel as the gel is being cast. Flexible fingers at each end of the row of teeth (the well-forming protrusions on the insert) serve to seal the insert against the spacers to reduce the risk of leakage of liquid around the insert.

These and other aspects, features, objects, and advantages of the invention will become more evident from the description that follows.

BRIEF DESCRIPTION OF THE DRAWINGS

FIG. 5a depicts a well-forming insert or "comb" in accordance with this invention. FIG. 5b shows the insert positioned between the spacers of a gel plate assembly.

DETAILED DESCRIPTION OF THE INVENTION AND SPECIFIC EMBODIMENTS

Figure 1:
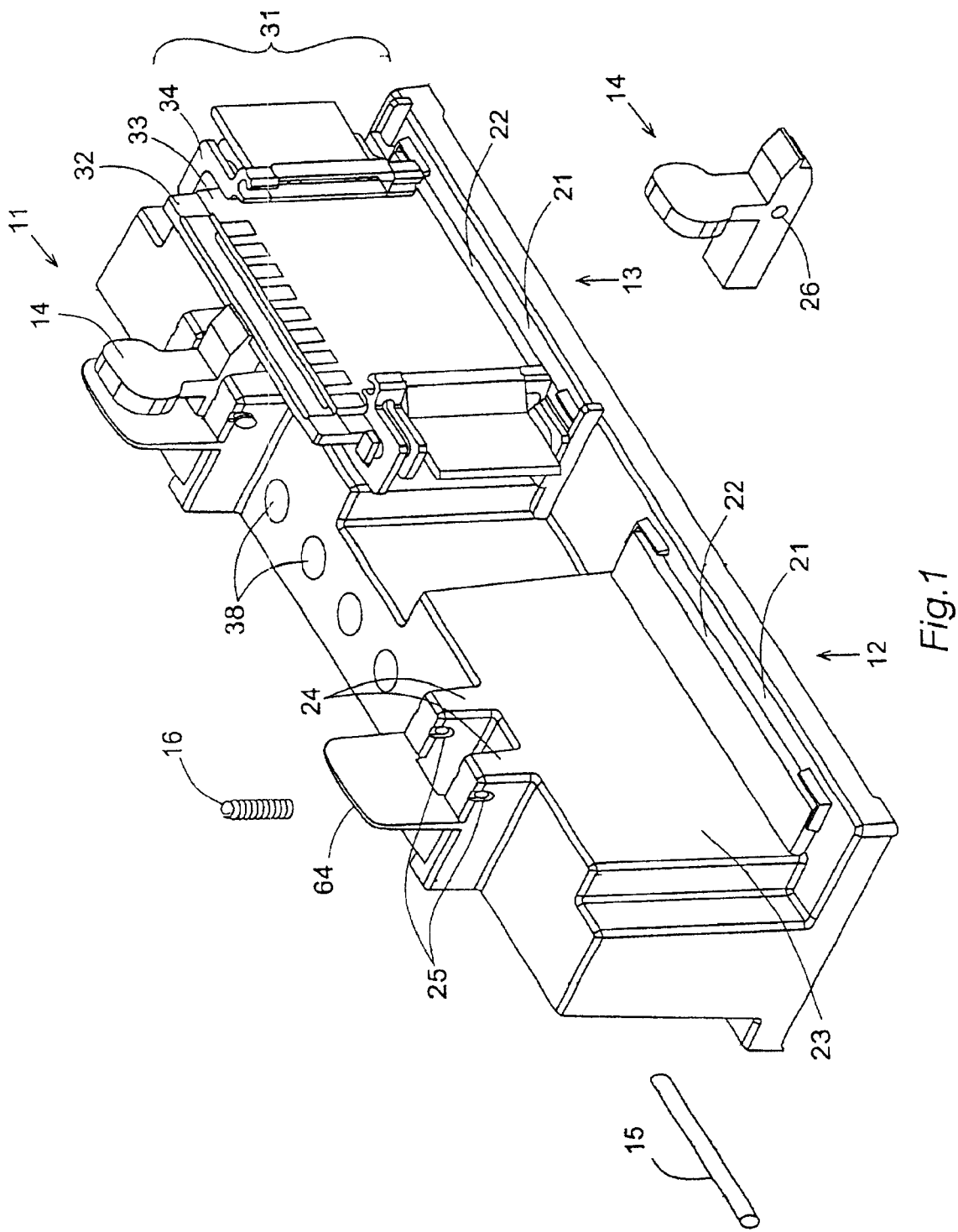
FIG. 1 is a perspective view, partially exploded, of a gel casting stand embodying features of the present invention.

In each of its several aspects, this invention can be implemented in a wide range of embodiments differing in structure, shape, and manner of operation. For a better understanding of the features that are common to these various embodiments, however, the following description will focus on the specific examples that are shown in the drawings. These are only illustrative, however.

The perspective view in FIG. 1 is that of a slab gel casting system that incorporates several aspects of the invention, illustrating how various features and parts fit together and coact. The system of FIG. 1 is designed for the casting of two slab gels independently on a single support rack 11 with left and right mounting stations 12, 13 in a side-by-side arrangement. The left mounting station 12 is shown empty, i.e., without a gel plate assembly, and with certain parts separated from the support rack to more clearly show the structure of the rack. The separated parts are the pivoting notched clamp 14, a pin 15 to secure the notched clamp to the support rack, and a coil spring 16 to bias the notched clamp, all of which are described in more detail below.

The gel enclosures to be used in the gel casting system of this and the succeeding drawings are any of the wide variety of gel plate assemblies used in slab electrophoresis, generally consisting of two flat rectangular plates separated by spacers between the plates along the opposing side edges of the plates, the spacers defining both the thickness of the gel due to their own thickness and the width of the gel due to the distance between the spacers. The spacers may be bonded to or molded as part of the surface of one of the two plates or separate strips of spacing material inserted between the flat plates. An illustrative gel plate assembly of this type is more visible in succeeding drawings and is further described in the descriptions of those drawings.

Components made visible on the left mounting station 12 include a floor 21 to support the bottom edge of the gel enclosure, a flat rectangular gasket 22 resting on the floor, and a vertical wall 23 against which the back of the gel enclosure rests. Extending upward from the top of the vertical wall are a pair of brackets 24 for mounting the notched clamp 14 to the support rack. Mounting is achieved by the pin 15 which passes through holes 25 in the brackets and a hole 26 in the notched clamp.

The right mounting station 13 is identical to the left mounting station 12 and is shown with the notched clamp 14 installed, together with a gel plate assembly 31 which includes a pair of flat rectangular glass plates 32, 33 of unequal height, the rear plate 32 having an upper edge extending above the upper edge of the forward plate 33. The two vertical side edges of the rear plate are slightly thicker than the central portion of the plate, forming raised platforms to serve as spacers for the forward plate, leaving a gap between the two plates for casting the gel. The gel plate assembly 31 also includes a clamping frame 34 that secures the two plates together to form fluid-tight closures along their side edges. The upper edge of the rear plate 32 is engaged by the notched clamp 14, which presses the rear plate and hence the entire gel plate assembly downward against the gasket to form a fluid-tight closure. The bottom and sides of the gel plate assembly are thus closed off, and a gel-forming solution can be poured into the space between the glass plates through the opening at the top between the two plates of unequal height.

A feature included in the support rack for added convenience is a row of holes 38 for holding tubes for samples or reagents. This makes the casting system a compact unit that serves multiple functions.

Figure 2:
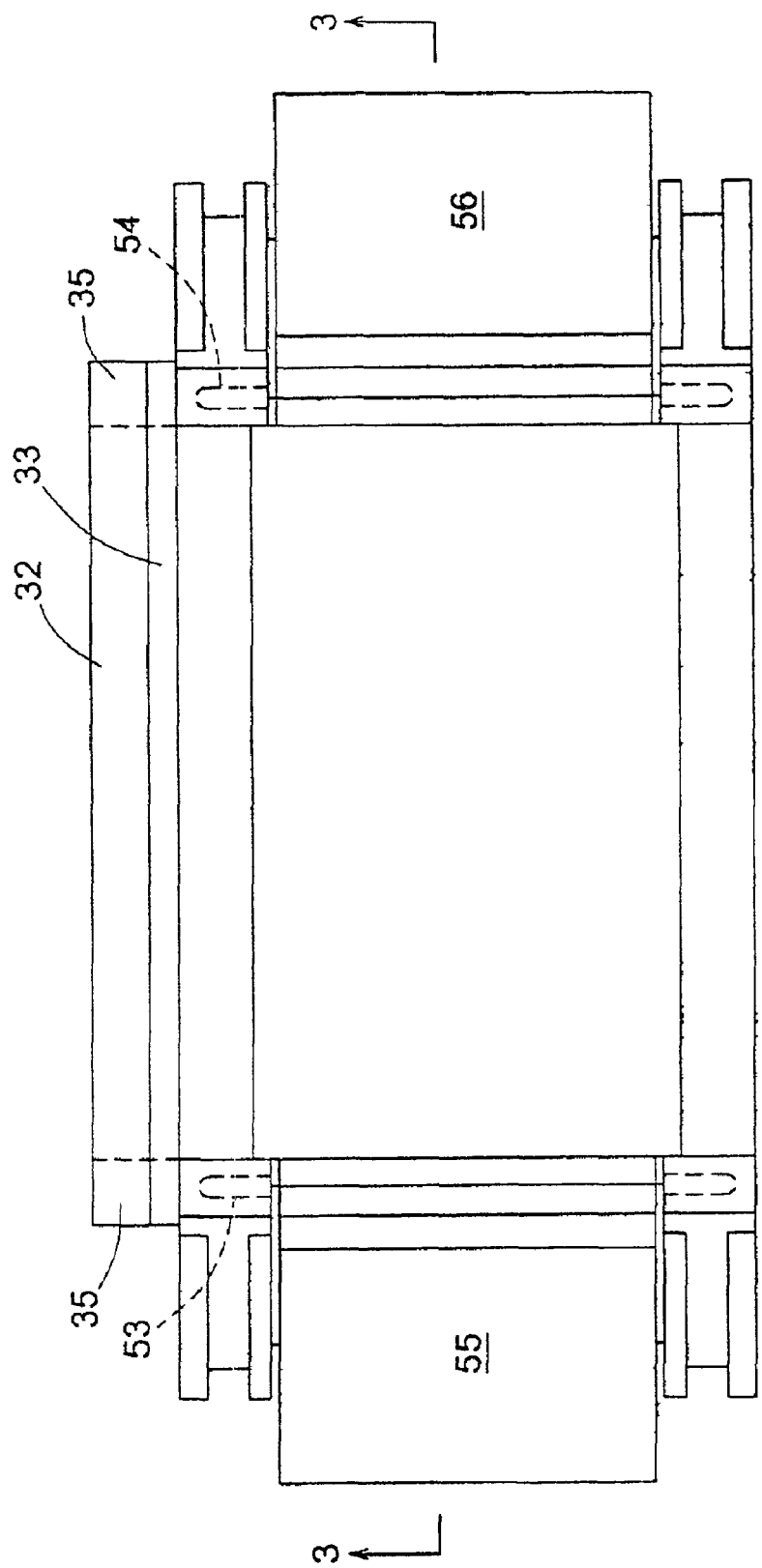
FIG. 2 is a front elevation view of a clamping frame for a gel plate assembly in accordance with this invention, identical to that shown mounted to the casting stand in FIG. 1.
Figure 3:
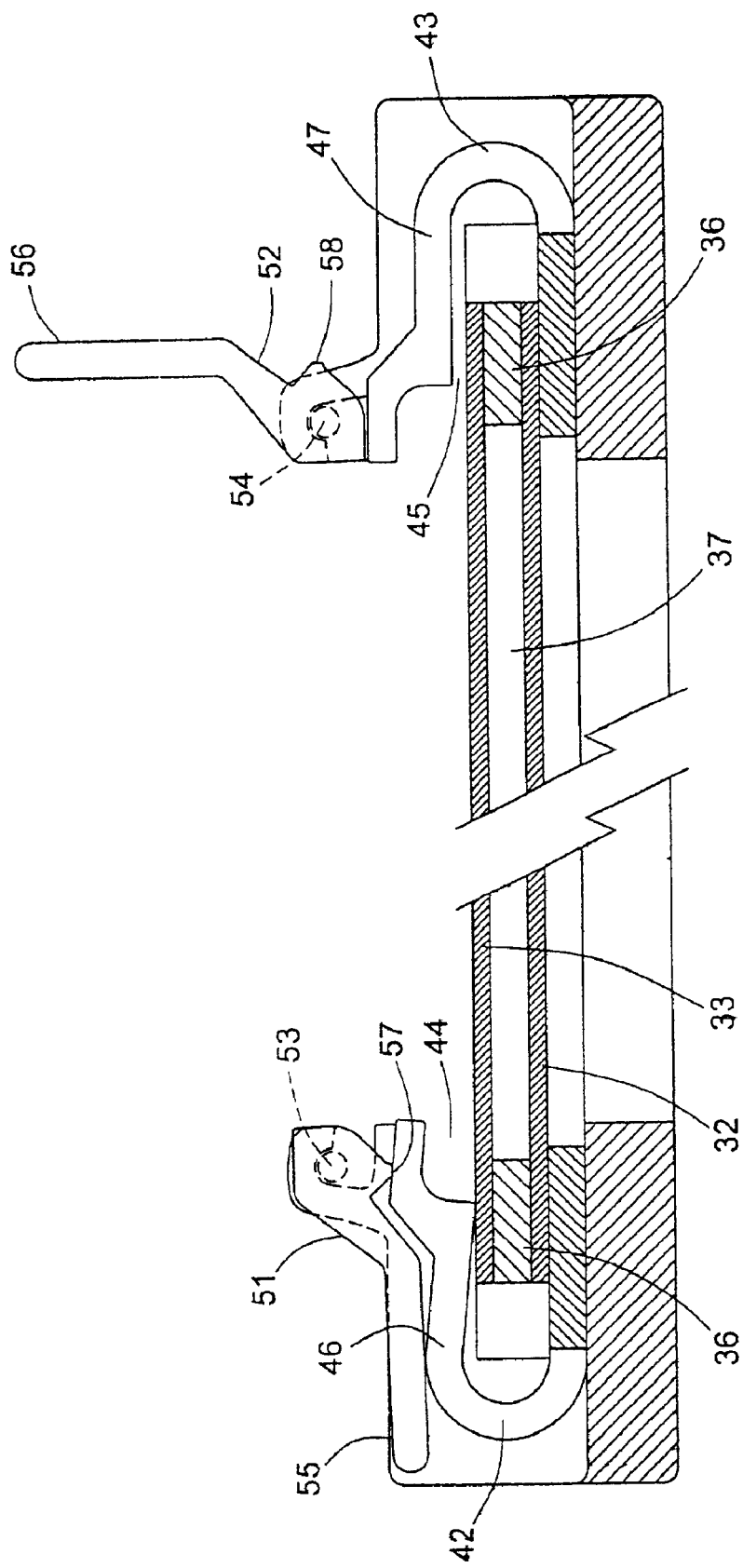
FIG. 3 is a cross section of the clamping frame and gel plate assembly of FIG. 2, taken along the line 3—3 of FIG. 2.

Detailed views of the gel plate assembly and clamping frame are seen in the front elevation view of these components in FIG. 2 and the cross section view of FIG. 3. The two glass plates 32, 33 are visible in both drawings. The spacers are shown in FIG. 2 as raised platforms 35 integrated into the structure of the rear plate 32 along the two side edges of the plate. FIG. 3 shows the spacers as separate strips 36. In either case, the spacers define a gap 37, visible in FIG. 3, to serve as the gel space. The clamping frame is a four-sided rectangular frame 41 open at the center, with retaining members 42, 43 (FIG. 3) along each of the two side edges. The retaining members have C-shaped profiles whose concave sides (referred to herein as channels or grooves 44, 45) face toward the center of the frame and each other. The grooves are large enough to loosely receive the side edges of the two glass plates with a spacer in between, and glass plates and spacers can thus be inserted into the retaining members from one end and slid along the lengths of the grooves until fully inserted. The length of each retaining member is preferably more than half the length of the side edge (ie., the height) of the shorter glass plate.

The outer walls 46, 47 of the retaining members are bendable and resilient. The wall 47 shown on the right side of FIG. 3 is in a relaxed condition, leaving the groove wide enough to allow free movement of the glass plates and spacer within the groove, while the wall 46 on the left side of the drawing is bent or distorted inward to contact the forward glass plate 33 and press the plates and spacer against each other. The inward bending and relaxation of the two bendable walls are controlled by the positions of two lever-operated cams 51, 52, each mounted to the frame in a rotatable manner by pins 53, 54 (shown in dashed lines). The lever 55 on the left cam is shown in a lowered position in which the cam itself 57 engages the bendable wall 46 pressing the wall against the glass plates. The lever 56 on the right cam has been rotated to a raised position, rotating the cam 58 out of contact with the bendable wall 47 and thereby releasing the wall from the glass plates. Each cam preferably extends substantially the full length of the corresponding bendable wall.

Figure 4:
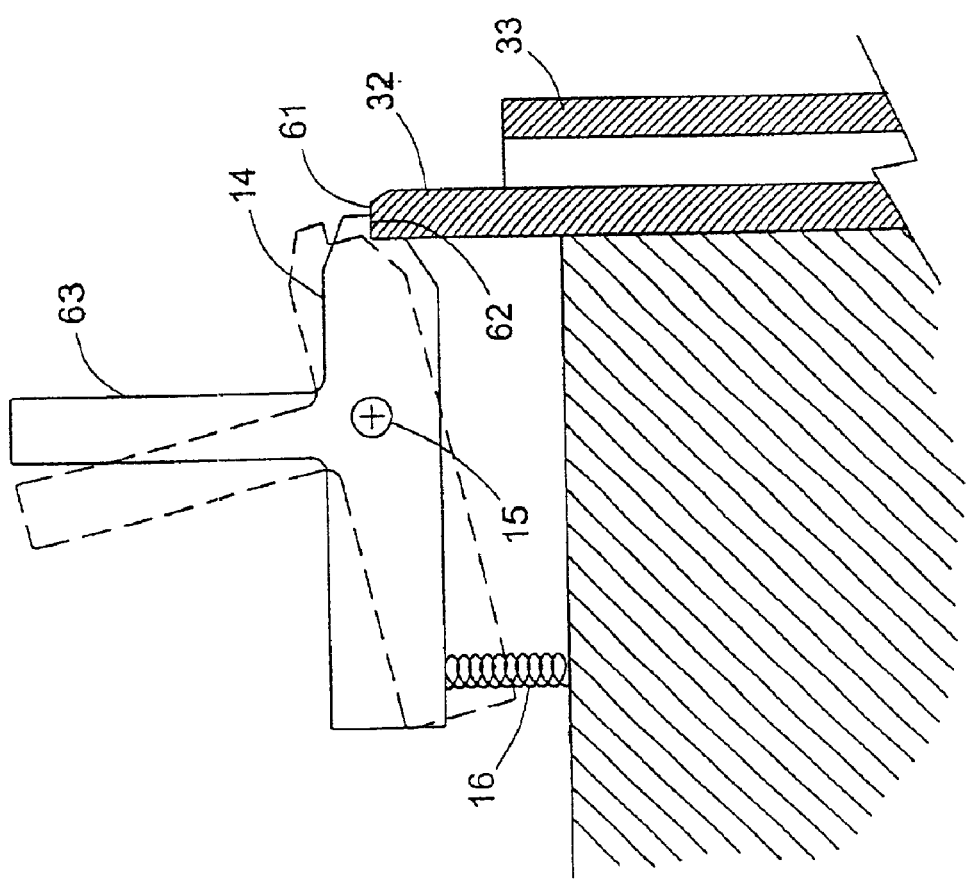
FIG. 4 is a side view of a notched clamp in accordance with this invention, the clamp being one of the components shown in the perspective view of FIG. 1.

FIG. 4 offers an enlarged view of the notched clamp 14 and its operation. The clamp, represented in solid lines, is in engagement with the upper edge 61 of the rear glass plate 32, the corner of the upper edge fitting within the notch 62 in the clamp which presses the glass plates downward against the gasket 22 (shown in FIG. 1). When the clamp is rotated around the mounting pin 15 to the position shown in dashed lines, the pressure is released. The spring 16 biases the clamp toward the clamping position (solid lines). Manual operation of the clamp is facilitated by the finger tab 63. This tab, in conjunction with the stationary finger tab 64 (FIG. 1) on the support rack permits easy engagement and release of the notched clamp 14 by simply squeezing the tabs together (and thereby compressing the coil spring 16) to open the clamp and releasing them to close the clamp and engage the gel plate assembly.

An additional feature or aspect of the present invention is a self-sealing insert for forming sample wells in the gel as the gel is being cast. Well-forming inserts are commonly referred to in patents and other literature as "templates" or "combs," the latter term reflecting the comb-like shape of the insert due to the teeth-like projections or protrusions that define the number, spacing and shape of the wells. The insert fits inside the gap between the glass plates and is placed along the upper edge of the gap with the teeth extending into the gel solution. When the gel sets, the insert is removed and the voids left by the teeth serve as wells for the placement of liquid samples to be separated by the electrophoretic analysis. The teeth may be of any shape but at most often rectangular and regularly spaced. Typical teeth are of the dimensions 0.20 inch (0.51 cm)×0.40 inch (1.02 cm), spaced apart by a distance of 0.11 inch (0.28 cm).

An illustration of an insert incorporating the novel features of the present invention appears in FIGS. 5a and 5b. FIG. 5a shows the insert entirely separate from the gel plate assembly. The insert consists of a flat strip 66 of solid, substantially rigid material with a row of teeth 67 of identical shape and equal spacing, extending perpendicularly from one side of the strip. While the insert shown in the drawing contains eight teeth, the number of teeth is not critical and inserts with different numbers of teeth (such as five, nine, ten, or fifteen) can be used as well. At the two extremities of the row are outwardly angled protrusions or fingers 68, 69. Each of these protrusions is flexible and resiliently bendable inward toward the remaining teeth. When the insert is placed between the glass plates and between the spacers 36, as shown in FIG. 5b, the end fingers 68, 69 are distorted from their relaxed condition and press against the inner edges of the spacers 36 to hold the insert in place and to form a lateral seal. Gel-forming solution that is placed in the gap between the glass plates is thus prevented from spillage around the ends of the insert by capillary action or when the gel plate assembly is lifted or handled.

Once the gel is cast, the plates and spacers with the gel in between can be removed from the support rack and from the clamping frame, and are then readily transferred to any electrophoresis cell appropriately sized to accept the assembled plates. One example of such as cell is the "Mini-PROTEAN® 3" Mini Vertical Electrophoresis System, a product of, and commercially available from, Bio-Rad Laboratories, Inc., of Hercules, Calif., USA. A description of this type of cell is found in U.S. Pat. No. 5,632,877 ("Rapid Assembly Electrophoresis Cell for Slab Gels," D. L. Van Atta, inventor, issued May 27, 1997).

The foregoing is offered primarily for purposes of illustration. It will be readily apparent to those skilled in the art that the configurations, relative dimensions, operating procedures and other parameters of this invention can be further modified or substituted in various ways without departing from the spirit and scope of the invention.

What is claimed is:

1. A casting stand for holding a rectangular slab gel enclosure having a bottom opening and securing said enclosure in a vertical position for casting a gel in said enclosure, said casting stand comprising:

a support rack having a floor sized to cover said bottom opening and a vertical wall extending upward from said floor;

a notched member pivotally mounted to said support rack above said floor, said notched member having a notch therein to receive an upper edge of said enclosure when said enclosure is resting against said vertical wall, said notched member capable of rotation between a clamping position in which said enclosure is received within said notch when said bottom opening is pressed against said floor, and an open position in which said notch is raised to release said enclosure from pressure against said floor and to thereby permit insertion and removal of said enclosure from said support rack, said notched member being spring-loaded to bias said notched member toward said clamping position.

2. A casting stand in accordance with claim 1 further comprising a gasket sized to cover said floor.

3. A casting stand in accordance with claim 1 in which said notched member comprises a tab accessible for manual manipulation to rotate said notched member between said clamping position and said open position.

4. A casting stand in accordance with claim 1 in which said tab is defined as a movable tab, and said casting stand further comprises a stationary tab extending from said support rack at a location adjacent to where said notched member is pivotally mounted to said support rack, said stationary and movable tabs arranged such that manually pressing said movable tab against said stationary tab will cause said notched member to be drawn from said clamping position to said open position while release of said movable tab will return said notched member into said clamping position.

* * * * *